United States Patent
Li et al.

(10) Patent No.: US 12,377,027 B2
(45) Date of Patent: Aug. 5, 2025

(54) GRADIENT RESIN, PREPARATION METHOD THEREFOR AND USE THEREOF

(71) Applicant: AIDITE (QINHUANGDAO) TECHNOLOGY CO., LTD., Hebei (CN)

(72) Inventors: Hongwen Li, Hebei (CN); Chunmei Qiao, Hebei (CN); Wendong Xu, Hebei (CN); Qianqian Liu, Hebei (CN); Xiaoran Guo, Hebei (CN)

(73) Assignee: AIDITE (QINHUANGDAO) TECHNOLOGY CO., LTD., Hebei (CN)

( * ) Notice: Subject to any disclaimer, the term of this patent is extended or adjusted under 35 U.S.C. 154(b) by 188 days.

(21) Appl. No.: 17/925,764

(22) PCT Filed: Oct. 23, 2020

(86) PCT No.: PCT/CN2020/123042
§ 371 (c)(1),
(2) Date: Nov. 16, 2022

(87) PCT Pub. No.: WO2022/067909
PCT Pub. Date: Apr. 7, 2022

(65) Prior Publication Data
US 2023/0181428 A1    Jun. 15, 2023

(30) Foreign Application Priority Data
Sep. 30, 2020   (CN) .......................... 202011065904.4

(51) Int. Cl.
| | | |
|---|---|---|
| *A61K 6/884* | (2020.01) | |
| *A61K 6/78* | (2020.01) | |
| *A61K 6/887* | (2020.01) | |
| *A61K 6/889* | (2020.01) | |
| *A61K 6/891* | (2020.01) | |
| *B29C 43/00* | (2006.01) | |
| *B32B 7/023* | (2019.01) | |
| *B32B 27/20* | (2006.01) | |
| *C08J 3/20* | (2006.01) | |
| *C08K 13/02* | (2006.01) | |
| *B29K 105/00* | (2006.01) | |
| *C08K 3/22* | (2006.01) | |
| *C08K 5/42* | (2006.01) | |

(52) U.S. Cl.
CPC ................ *A61K 6/889* (2020.01); *A61K 6/78* (2020.01); *A61K 6/887* (2020.01); *A61K 6/891* (2020.01); *B32B 7/023* (2019.01); *C08J 3/203* (2013.01); *C08K 13/02* (2013.01); *B29C 43/003* (2013.01); *B29K 2105/251* (2013.01); *B29K 2995/0021* (2013.01); *C08J 2325/06* (2013.01); *C08J 2333/12* (2013.01); *C08J 2359/00* (2013.01); *C08K 2003/2241* (2013.01); *C08K 2003/2265* (2013.01); *C08K 2003/2289* (2013.01); *C08K 5/42* (2013.01); *C08K 2201/014* (2013.01)

(58) Field of Classification Search
CPC .......... A61K 6/884; A61K 6/889; A61K 6/78; B32B 7/023; B32B 27/20; C08K 13/02; B29K 2995/0021
See application file for complete search history.

(56) References Cited

U.S. PATENT DOCUMENTS

| | | | |
|---|---|---|---|
| 2,454,847 A | 11/1948 | Slack, Jr. | |
| 2020/0268616 A1 | 8/2020 | Wang et al. | |

FOREIGN PATENT DOCUMENTS

| | | |
|---|---|---|
| CN | 103273713 A | 9/2013 |
| CN | 105362084 A | 3/2016 |
| CN | 108078789 A | 5/2018 |
| CN | 108578251 A | 9/2018 |
| CN | 109589270 A | 4/2019 |
| GB | 514830 A | 11/1939 |
| GB | 638981 A | 6/1950 |
| JP | H1085237 A | 4/1998 |
| JP | H10323353 A | 12/1998 |

OTHER PUBLICATIONS

International Search Report for PCT/CN2020/123042 mailed Jul. 13, 2021.
Written Opinion for or PCT/CN2020/123042 mailed Jul. 13, 2021.
Chinese Office action dated May 12, 2021 from corresponding Chinese Application No. 202011065904.4with English translation.
Supplemental European Search report for corresponding EP App. No. 20955929.3 dated Mar. 19, 2024.

*Primary Examiner* — Joanna Pleszczynska
(74) *Attorney, Agent, or Firm* — Sandberg Phoenix & von Gontard P.C.

(57) ABSTRACT

Disclosed are a gradient resin, a preparation method therefor and the use thereof. The gradient resin of the present application is formed by fusing different layers with color transition changes, wherein the color transition change between the two adjacent layers is in the range of 0.1% to 20%. The gradient resin is composed of, by mass percentage, 98%-99.99% of a resin powder and 0.01%-2% of a pigment.

16 Claims, No Drawings

GRADIENT RESIN, PREPARATION METHOD THEREFOR AND USE THEREOF

CROSS-REFERENCE TO RELATED APPLICATIONS

This application is the US National Stage under 35 USC § 371 of International Application No. PCT/CN2020/123042, filed 23 Oct. 2020 which claims priority to Chinese Application No. 202011065904.4 filed 30 Sep. 2020, both of which are incorporated herein by reference.

TECHNICAL FIELD

The present application belongs to the technical field of gradient resins, and relates to a gradient resin, a preparation method therefor and use thereof, for example, a gradient aesthetic dental resin material, a preparation method therefor and use thereof, and in particular, a natural-transition gradient aesthetic dental resin material, a preparation method therefor and use thereof.

BACKGROUND

Currently, with the improvement of people's living standards and the progress of science and technology, there are increasing requirements for dental aesthetic restoration, which thus give a rise to the requirements for multi-layer gradient resin. The CAD/CAM gradient dental PMMA resin is suitable for temporary restorations: single crown, bridge, full mouth reconstruction, etc., and has the advantages of high glossiness and good luminous transmittance, but the existing process is mostly to prepare semi-solid sheets with different colors firstly, and then stack all the sheets in the mold according to the color order for a hot-press molding, and the products produced by this molding process generally have obvious interlayer boundaries and unnatural color transitions.

CN103273713B discloses a four-layer-color synthetic resin block and a preparation method therefor. The four-layer-color synthetic resin block is sequentially composed of structures of four layers, and the structure of each layer includes compositions as follows: poly(methyl methacrylate), iron oxide red, iron oxide black, iron oxide yellow, titanium white, methyl methacrylate and ethylene glycol dimethacrylate. The preparation method includes the steps as follows: a poly(methyl methacrylate) powder is dried at a temperature of 80-90° C.; materials used for the four layers are prepared in proportion respectively, and the material used for each layer is required to be mixed uniformly and kneaded until a dough stage, so that a plastic dough material is formed; four layers of the plastic dough materials are subjected to a hot-press molding and bonded together in sequence in a mold, a hot-press temperature is 110-130° C., and a hot-press time is 10-20 min; the four-layer-color synthetic resin block after hot-press molding is subjected to a heat treatment at a temperature of 80-90° C. for 10-12 h, so as to obtain the four-layer-color synthetic resin block product. A dental model or temporary crown bridge, which is processed through this invention, is natural and vivid in color. In this patent, poly(methyl methacrylate), methyl methacrylate and ethylene glycol dimethacrylate were used to prepare the materials used for the four layers respectively, mixed uniformly, kneaded to the dough stage, and then subjected to the hot-press molding in sequence to obtain the four-layer-color synthetic resin block. However, such four-layer-color resin has the problems of serious layer stratification and unnatural color transition, which affect the use effect during use.

CN108078789A discloses a preparation method for a multi-color integrated dental restoration material, relates to the technical field of false tooth restoration materials, and solves the problem that the restoration layer of the existing multi-color restoration material is easily separated during processing. The method includes the following steps: one, various compositions are added to multiple containers, the temperature is controlled at 10-25° C., and the compositions are stirred for 3-5 min, mixed uniformly and then allowed to stand for 10-20 min, so that the mixtures are turned into a thick gel form, and the mixtures with different colors are obtained; two, the mixtures with different colors are placed in an environment at less than or equal to −15° C. for cooling, so as to obtain semi-cured mixtures with different colors; three, multiple semi-cured mixtures with different colors are taken out and stacked in a mold with openings at the two ends, the mold is sealed by moving an upper mold and a lower mold towards each other, and the mixtures are heated to 40-80° C., pressure-polymerized, cured-molded, and removed from the mold to obtain the multi-color integrated dental restoration material. The gradient-color dental restoration material prepared by this invention is high in interface strength and material consistency, good in impact resistance and high in manufacturing precision. In this patent, poly(methyl methacrylate), methyl methacrylate, a curing agent and a pigment are mixed and stirred at a certain temperature to form the thick gel form mixture with different colors, and then cooled at −15° C. to form the semi-cured mixture with different colors, and the semi-cured mixture is pressure-polymerized to obtain the multi-color integrated dental restoration material. The patent uses a two-step polymerization method to prepare dental restoration materials, which can precisely control the shape, thickness and color of the contact interface between adjacent layers, but the product boundary of this patent is still obvious, and the interlayer transition is unnatural.

The common method in the prior art is to knead the different layers to the dough stage, and then subject the four layers of the plastic dough materials to a hot-press molding at 110° C.-130° C. and bond them together in sequence in a mold to obtain the four-layer-color synthetic resin block. Or the resin monomers are frozen at −15° C.-0° C. for more than or equal to 4 hours to obtain the gel-form materials, and the gel-form materials are poured into the mold according to the order of color shade separately, allowed to stand for more than or equal to 12 h at room temperature, and cured to obtain the dental restoration material. The gradient resins obtained by the above methods both have unnatural interlayer transition, the teeth can be found to be a layer stratification state under the sunlight, and the boundary line can be clearly seen, resulting in poor aesthetic effect of the cut teeth.

At present, it is difficult for multi-layer gradient resin materials to achieve natural interlayer transition without stratification. Therefore, it is necessary to develop a novel multi-layer gradient resin material with natural interlayer transition without stratification.

SUMMARY

The present application is to provide a gradient resin, a preparation method therefor and use thereof. The gradient resin prepared in the present application has natural color, the layers merge into each other, no transition boundary can be found between layers, and the performances of luminous transmittance and flexural strength are excellent.

A first object of the present application is to provide a gradient resin, and in order to achieve this object, the present application adopts the technical solutions below.

A gradient resin is provided, and the gradient resin is formed by merging different layers with color transition change, in which the color transition change range between two adjacent layers is 0.1-20%, and by mass percentage, the gradient resin is composed of 98-99.99% of a resin powder and 0.01-2% of a pigment.

It should be noted that the color transition change between two adjacent layers refers to a mass content change of the pigment in the gradient resin raw materials of two adjacent layers.

The gradient resin of the present application is prepared by mixing and hot-pressing the resin powder and the pigment without adding with any monomer or crosslinking agent; since the resin prepared by this method can be merged well between layers and has gentle interlayer color transition, the resin product has no layer stratification, and the color transition is natural.

It is found in the present application by analyzing the layer stratification and transition that, when the interlayer color transition is less than 20%, the product exhibits a good color transition effect, and no interlayer boundary can be seen. The color transition change may be 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20%, etc.; optionally, when the interlayer color transition is less than 7%, the product obtains the best color transition effect. By mass percentage, the mass percentage of the resin powder may be 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, 99.99%, etc., and the mass percentage of the pigment may be 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2%, etc.

A particle size of the resin powder is 0.1-200 μm, such as 0.1 μm, 0.5 μm, 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm or 200 μm, etc.; the particle size is optionally 30-150 μm, more optionally 40-100 μm.

A molecular mass of the resin powder is 100000-1000000, such as 100000, 200000, 300000, 400000, 500000, 600000, 700000, 800000, 900000 or 1000000, etc.; the molecular mass is optionally 300000-700000, more optionally 400000-600000.

The resin powder includes any one or a mixture of at least two of poly(methyl methacrylate), poly(ethyl methacrylate), poly(propyl methacrylate), poly(n-butyl methacrylate), poly(isobutyl methacrylate), poly(hexyl methacrylate), poly(dicyclopentenyl methacrylate), poly(tetrahydrofurfuryl methacrylate), poly(2-hydroxyethyl methacrylate), poly(glycidyl methacrylate), poly(lauryl methacrylate), poly(cyclohexyl methacrylate), poly(benzyl methacrylate), poly(allyl methacrylate), poly(2-ethoxyethyl methacrylate), methoxy polyethylene glycol methacrylate, poly(glycerol methacrylate), poly(isobornyl methacrylate), polyvinyl chloride, polystyrene, polyoxymethylene, polyacetaldehyde and polyurethane.

The pigment includes any one or a mixture of at least two of zirconium vanadium yellow, cerium praseodymium yellow, tartrazine, ferric oxide yellow, chrome yellow, sunset red, iron oxide red, erbium oxide, titanium dioxide, cobalt oxide, chromium oxide, iron oxide brown, iron oxide black and carbon black.

A second object of the present application is to provide a preparation method for the gradient resin according to the first object, including the following steps:
1) preparing colored powders: weighing and uniformly mixing the pigment and the resin powder for preparing colored powders with different colors according to respective color formulas, and weighing and proportioning the colored powders for each layer according to a layer configuration;
2) spreading the materials: adding the colored powders with different colors obtained in step 1) into a molding mold in sequence, spreading one colored powder flat out in the molding mold, then adding another colored powder of the next layer and spreading the colored powder flat out until all the colored powders have been added; and
3) performing a press molding: subjecting the mold to a hot-press molding, and taking the mold out after cooling, so as to obtain the gradient resin.

In step 2), the color transition change range between two adjacent layers is 0.1-20%.

Optionally, in step 3), a temperature of the hot-press molding is 60-220° C.; for example, the temperature of the hot-press molding is 60° C., 70° C., 80° C., 90° C., 100° C., 110° C., 120° C., 130° C., 140° C., 150° C., 160° C., 170° C., 180° C., 190° C., 200° C., 210° C., or 220° C., etc., optionally 100-180° C., more optionally 120-160° C.

Optionally, in step 3), a pressure of the hot-press molding is 1-20 MPa; for example, the pressure of the hot-press molding is 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, etc., optionally 4-15 MPa, and more optionally 8-12 MPa.

Optionally, the preparation method further includes a pretreatment step for the resin powder before step 1);

Optionally, the pretreatment includes drying, and a temperature of the drying is 80-100° C.; for example, the temperature of the drying is 80° C., 85° C., 90° C., 95° C., or 100° C., etc.; a time of the drying is 1-3 h; for example, the time of the drying is 1 h, 1.5 h, 2 h, 2.5 h, or 3 h, etc.

As an optional solution of the present application, a preparation method for the gradient resin includes the following steps:
1) preparing colored powders: drying the resin powder at 80-100° C. for 1-3 h, weighing and uniformly mixing the pigment and the resin powder for preparing colored powders with different colors according to respective color formulas, and weighing and proportioning the colored powders for each layer according to a layer configuration;
2) spreading the materials: adding the colored powders with different colors obtained in step 1) into a molding mold in sequence, spreading one colored powder flat out in the molding mold, then adding another colored powder of the next layer and spreading the colored powder flat out until all the colored powders have been added, in which the color transition change range between two adjacent layers is 0.1-20%; and
3) performing a press molding: subjecting the materials to be molded to a hot-press molding in the mold, and removing the mold after molding, so as to obtain the gradient resin with natural interlayer transition and no color stratification, in which an optional press method is a hot-press molding, and the mold is removed after cooling, a temperature of the hot-press molding is 60-220° C., and a pressure of the hot-press molding is 1-20 MPa.

A third object of the present application is to use of the gradient resin according to the first object, in which the gradient resin is used in preparing a gradient dental restoration, and the aesthetic effect of the teeth is excellent.

Compared with the prior art, the beneficial effects of the present application are as follows.

The gradient resin of the present application has a simple preparation method; the gradient resin is prepared by mixing and hot-pressing the resin powder and the pigment without adding with any monomer or crosslinking agent; since the resin prepared by this method can be merged well between layers and has gentle interlayer color transition, the prepared gradient resin product has no layer stratification, the color transition is natural, the layers merge into each other, no transition boundary can be found between layers, the interlayer color transition change range is 0.1-20%, and it is invisible to the naked eye; the prepared gradient resin has a luminous transmittance of more than or equal to 50%, a flexural strength of more than 100 MPa, a Vickers hardness of more than 20 HV, a water absorption value of less than 25 $\mu g/mm^3$, and a solubility value of less than 5 $\mu g/mm^3$. The gradient resin prepared in the present application has excellent aesthetic effect when used in dental materials.

DETAILED DESCRIPTION

The technical solutions of the present application are further described below through specific embodiments.

Unless otherwise specified, various raw materials of the present application can be purchased commercially or prepared according to conventional methods in the art.

Example 1

A preparation method for the gradient resin of this example includes the following steps:
(1) raw material drying: a poly(methyl methacrylate) powder was dried at 90° C. for 2 h;
(2) colored powders preparation: the pigment and the poly(methyl methacrylate) powder were mixed uniformly according to color formulas, and each layer was required to have a uniform color without material spots, in which a color transition difference of each layer was 5%;
(3) spreading the colored powders: the colored powder of the first layer was added into a molding mold and spread flat out, and the materials were spread layer by layer until all the colored powders have been spread; and
(4) press molding: press molding was performed without exceeding the pressure that the materials were able to withstand, a temperature of a hot-press molding was 150° C., and a time was 60 min. After the hot-press molding, the materials were cooled to room temperature under the same pressure.

In the method, mass percentages of each composition of the materials are described below separately:
the first layer: poly(methyl methacrylate): 99.9354%, iron oxide red: 0.00131%, tartrazine: 0.01414%, titanium dioxide: 0.04687%, cobalt oxide: 0.00232%;
the second layer: poly(methyl methacrylate): 99.9386%, iron oxide red: 0.00124%, tartrazine: 0.01343%, titanium dioxide: 0.04453%, cobalt oxide: 0.00220%;
the third layer: poly(methyl methacrylate): 99.9418%, iron oxide red: 0.00117%, tartrazine: 0.01273%, titanium dioxide: 0.04218%, cobalt oxide: 0.00209%;
the fourth layer: poly(methyl methacrylate): 99.9451%, iron oxide red: 0.00111%, tartrazine: 0.01202%, titanium dioxide: 0.03984%, cobalt oxide: 0.00197%;
the fifth layer: poly(methyl methacrylate): 99.9483%, iron oxide red: 0.00104%, tartrazine: 0.01131%, titanium dioxide: 0.03750%, cobalt oxide: 0.00186%;
the sixth layer: poly(methyl methacrylate): 99.9515%, iron oxide red: 0.00098%, tartrazine: 0.01061%, titanium dioxide: 0.03515%, cobalt oxide: 0.00174%;
the seventh layer: poly(methyl methacrylate): 99.9548%, iron oxide red: 0.00091%, tartrazine: 0.00990%, titanium dioxide: 0.03281%, cobalt oxide: 0.00162%;
the eighth layer: poly(methyl methacrylate): 99.9580%, iron oxide red: 0.00085%, tartrazine: 0.00919%, titanium dioxide: 0.03047%, cobalt oxide: 0.00151%;
the ninth layer: poly(methyl methacrylate): 99.9612%, iron oxide red: 0.00078%, tartrazine: 0.00848%, titanium dioxide: 0.02812%, cobalt oxide: 0.00139%;
the tenth layer: poly(methyl methacrylate): 99.9644%, iron oxide red: 0.00072%, tartrazine: 0.00778%, titanium dioxide: 0.02578%, cobalt oxide: 0.00128%;
the eleventh layer: poly(methyl methacrylate): 99.9677%, iron oxide red: 0.00065%, tartrazine: 0.00707%, titanium dioxide: 0.02344%, cobalt oxide: 0.00116%;
the twelfth layer: poly(methyl methacrylate): 99.9709%, iron oxide red: 0.000585%, tartrazine: 0.00636%, titanium dioxide: 0.02109%, cobalt oxide: 0.00104%;
the thirteenth layer: poly(methyl methacrylate): 99.9741%, iron oxide red: 0.00052%, tartrazine: 0.00566%, titanium dioxide: 0.01875%, cobalt oxide: 0.00093%;
the fourteenth layer: poly(methyl methacrylate): 99.9774%, iron oxide red: 0.00046%, tartrazine: 0.00495%, titanium dioxide: 0.01640%, cobalt oxide: 0.00081%;
the fifteenth layer: poly(methyl methacrylate): 99.9806%, iron oxide red: 0.00039%, tartrazine: 0.00424%, titanium dioxide: 0.01406%, cobalt oxide: 0.00070%;
the sixteenth layer: poly(methyl methacrylate): 99.9838%, iron oxide red: 0.00033%, tartrazine: 0.00354%, titanium dioxide: 0.01172%, cobalt oxide: 0.00058%;
the seventeenth layer: poly(methyl methacrylate): 99.9871%, iron oxide red: 0.00026%, tartrazine: 0.00283%, titanium dioxide: 0.00937%, cobalt oxide: 0.00046%.

In the method, poly(methyl methacrylate) had a particle size of 40 $\mu m$ and a molecular mass of 500000.

Example 2

A preparation method for the gradient resin of this example includes the following steps:
(1) raw material drying: a polystyrene powder was dried at 90° C. for 2 h;
(2) colored powders preparation: the pigment and the poly(methyl methacrylate) powder were mixed uniformly according to color formulas, and each layer was required to have a uniform color without material spots, in which a color transition difference of each layer was 6%;

(3) spreading the colored powders: the colored powder of the first layer was added into a molding mold and spread flat out, and the colored powders were added layer by layer until all the colored powders have been spread; and
(4) press molding: press molding was performed without exceeding the pressure that the materials were able to withstand, a temperature of a hot-press molding was 160° C., and a time was 50 min. After the hot-press molding, the materials were cooled to room temperature under the same pressure.

In the method, mass percentages of each composition of the materials are described below separately:
the first layer: polystyrene: 99.9402%, iron oxide red: 0.00120%, ferric oxide yellow: 0.01352%, titanium dioxide: 0.04293%, cobalt oxide: 0.00214%;
the second layer: polystyrene: 99.9438%, iron oxide red: 0.00113%, ferric oxide yellow: 0.01271%, titanium dioxide: 0.04293%, cobalt oxide: 0.00214%;
the third layer: polystyrene: 99.9474%, iron oxide red: 0.00106%, ferric oxide yellow: 0.01190%, titanium dioxide: 0.03778%, cobalt oxide: 0.00188%;
the fourth layer: polystyrene: 99.9510%, iron oxide red: 0.00098%, ferric oxide yellow: 0.01109%, titanium dioxide: 0.03520%, cobalt oxide: 0.00175%;
the fifth layer: polystyrene: 99.9546%, iron oxide red: 0.00091%, ferric oxide yellow: 0.01028%, titanium dioxide: 0.03263%, cobalt oxide: 0.00163%;
the sixth layer: polystyrene: 99.9581%, iron oxide red: 0.00084%, ferric oxide yellow: 0.00946%, titanium dioxide: 0.03005%, cobalt oxide: 0.00150%;
the seventh layer: polystyrene: 99.9617%, iron oxide red: 0.00077%, ferric oxide yellow: 0.00865%, titanium dioxide: 0.02748%, cobalt oxide: 0.00137%;
the eighth layer: polystyrene: 99.9653%, iron oxide red: 0.00070%, ferric oxide yellow: 0.00784%, titanium dioxide: 0.02490%, cobalt oxide: 0.00124%;
the ninth layer: polystyrene: 99.9689%, iron oxide red: 0.00062%, ferric oxide yellow: 0.00703%, titanium dioxide: 0.02232%, cobalt oxide: 0.00111%;
the tenth layer: polystyrene: 99.9713%, iron oxide red: 0.00058%, ferric oxide yellow: 0.00649%, titanium dioxide: 0.02061%, cobalt oxide: 0.00103%;
the eleventh layer: polystyrene: 99.9749%, iron oxide red: 0.00050%, ferric oxide yellow: 0.00568%, titanium dioxide: 0.01803%, cobalt oxide: 0.00090%;
the twelfth layer: polystyrene: 99.9785%, iron oxide red: 0.00043%, ferric oxide yellow: 0.00487%, titanium dioxide: 0.01545%, cobalt oxide: 0.00070%;
the thirteenth layer: polystyrene: 99.9821%, iron oxide red: 0.00036%, ferric oxide yellow: 0.00406%, titanium dioxide: 0.01288%, cobalt oxide: 0.00064%;
the fourteenth layer: polystyrene: 99.9857%, iron oxide red: 0.00029%, ferric oxide yellow: 0.00324%, titanium dioxide: 0.01030%, cobalt oxide: 0.00051%;
the fifteenth layer: polystyrene: 99.9892%, iron oxide red: 0.00022%, ferric oxide yellow: 0.00243%, titanium dioxide: 0.00773%, cobalt oxide: 0.00039%;
the sixteenth layer: polystyrene: 99.9928%, iron oxide red: 0.00014%, ferric oxide yellow: 0.00162%, titanium dioxide: 0.00515%, cobalt oxide: 0.00026%;
the seventeenth layer: polystyrene: 99.9964%, iron oxide red: 0.00007%, ferric oxide yellow: 0.00081%, titanium dioxide: 0.00258%, cobalt oxide: 0.00013%.

In the method, the polystyrene powder had a particle size of 45 μm and a molecular mass of 400000.

Example 3

A preparation method for the gradient resin of this example includes the following steps:
(1) raw material drying: a polyoxymethylene resin powder was dried at 90° C. for 4 h;
(2) colored powders preparation: the pigment and the polyoxymethylene resin powder were mixed uniformly according to color formulas, and each layer was required to have a uniform color without material spots, in which a color transition difference of each layer was 20%;
(3) spreading the colored powders: the colored powder of the first layer was added into a molding mold and spread flat out, and the colored powders were spread layer by layer until all the colored powders for 17 layers have been spread; and
(4) press molding: press molding was performed without exceeding the pressure that the materials were able to withstand, a temperature of a hot-press molding was 160° C., and a time was 50 min. After the hot-press molding, the materials were cooled to room temperature under the same pressure.

In the method, mass percentages of each composition of the materials for each layer are described below separately:
the first layer: polyoxymethylene resin: 99.5825%, sunset red: 0.01260%, ferric oxide yellow: 0.11490%, titanium dioxide: 0.25830%, iron oxide black: 0.03170%;
the second layer: polyoxymethylene resin: 99.6660%, sunset red: 0.01008%, ferric oxide yellow: 0.09192%, titanium dioxide: 0.20664%, iron oxide black: 0.02536%;
the third layer: polyoxymethylene resin: 99.7495%, sunset red: 0.00756%, ferric oxide yellow: 0.06894%, titanium dioxide: 0.15498%, iron oxide black: 0.01902%;
the fourth layer: polyoxymethylene resin: 99.8330%, sunset red: 0.00504%, ferric oxide yellow: 0.04596%, titanium dioxide: 0.10332%, iron oxide black: 0.01268%;
the fifth layer: polyoxymethylene resin: 99.9165%, sunset red: 0.00252%, ferric oxide yellow: 0.02298%, titanium dioxide: 0.05166%, iron oxide black: 0.00634%.

In the method, the polyoxymethylene resin had a particle size of 60 μm and a molecular mass of 550000.

Example 4

This example differs from Example 1 in that the particle size of poly(methyl methacrylate) was 0.05 μm, and the others were the same as those of Example 1.

Example 5

This example differs from Example 1 in that the particle size of poly(methyl methacrylate) was 300 μm, and the others were the same as those of Example 1.

Example 6

This example differs from Example 1 in that the molecular mass of poly(methyl methacrylate) was 50000, and the others were the same as those of Example 1.

Example 7

This example differs from Example 1 in that the molecular mass of poly(methyl methacrylate) was 1500000, and the others were the same as those of Example 1.

Example 8

This example differs from Example 1 in that the resin powder is a polyether ether ketone powder, and the others were the same as those of Example 1.

Comparative Example 1

In this comparative example, the color transition change range between two adjacent layers was 0.05%, and the others were the same as those of Example 1. The specific composition of each layer was as follows:
- the first layer: poly(methyl methacrylate): 99.9354%, iron oxide red: 0.00131%, tartrazine: 0.01414%, titanium dioxide: 0.04687%, cobalt oxide: 0.00232%;
- the second layer: poly(methyl methacrylate): 99.9354%, iron oxide red: 0.00131%, tartrazine: 0.01413%, titanium dioxide: 0.04685%, cobalt oxide: 0.00232%;
- the third layer: poly(methyl methacrylate): 99.9354%, iron oxide red: 0.00131%, tartrazine: 0.01413%, titanium dioxide: 0.04682%, cobalt oxide: 0.00232%;
- the fourth layer: poly(methyl methacrylate): 99.9355%, iron oxide red: 0.00131%, tartrazine: 0.01412%, titanium dioxide: 0.04680%, cobalt oxide: 0.00232%;
- the fifth layer: poly(methyl methacrylate): 99.9355%, iron oxide red: 0.00131%, tartrazine: 0.01411%, titanium dioxide: 0.04678%, cobalt oxide: 0.00232%;
- the sixth layer: poly(methyl methacrylate): 99.9355%, iron oxide red: 0.00131%, tartrazine: 0.01410%, titanium dioxide: 0.04675%, cobalt oxide: 0.00231%;
- the seventh layer: poly(methyl methacrylate): 99.9356%, iron oxide red: 0.00131%, tartrazine: 0.01410%, titanium dioxide: 0.04673%, cobalt oxide: 0.00231%;
- the eighth layer: poly(methyl methacrylate): 99.9356%, iron oxide red: 0.00131%, tartrazine: 0.01409%, titanium dioxide: 0.04671%, cobalt oxide: 0.00231%;
- the ninth layer: poly(methyl methacrylate): 99.9356%, iron oxide red: 0.00130%, tartrazine: 0.01408%, titanium dioxide: 0.04668%, cobalt oxide: 0.00231%;
- the tenth layer: poly(methyl methacrylate): 99.9357%, red iron oxide: 0.00130%, tartrazine: 0.01408%, titanium dioxide: 0.04666%, cobalt oxide: 0.00231%;
- the eleventh layer: poly(methyl methacrylate): 99.9357%, red iron oxide: 0.00130%, tartrazine: 0.01407%, titanium dioxide: 0.04664%, cobalt oxide: 0.00231%;
- the twelfth layer: poly(methyl methacrylate): 99.9357%, iron oxide red: 0.00130%, tartrazine: 0.01406%, titanium dioxide: 0.04661%, cobalt oxide: 0.00231%;
- the thirteenth layer: poly(methyl methacrylate): 99.9357%, iron oxide red: 0.00130%, tartrazine: 0.01406%, titanium dioxide: 0.04659%, cobalt oxide: 0.00231%;
- the fourteenth layer: poly(methyl methacrylate): 99.9358%, iron oxide red: 0.00130%, tartrazine: 0.01405%, titanium dioxide: 0.04657%, cobalt oxide: 0.00230%;
- the fifteenth layer: poly(methyl methacrylate): 99.9358%, iron oxide red: 0.00130%, tartrazine: 0.01404%, titanium dioxide: 0.04654%, cobalt oxide: 0.00230%;
- the sixteenth layer: poly(methyl methacrylate): 99.9358%, red iron oxide: 0.00130%, tartrazine: 0.01403%, titanium dioxide: 0.04652%, cobalt oxide: 0.00230%;
- the seventeenth layer: poly(methyl methacrylate): 99.9359%, red iron oxide: 0.00130%, tartrazine: 0.01403%, titanium dioxide: 0.04650%, cobalt oxide: 0.00230%.

Comparative Example 2

In this comparative example, the color transition change range between two adjacent layers was 25%, and the others were the same as those of Example 1. The specific composition of each layer is as follows:
- the first layer: poly(methyl methacrylate): 99.9354%, iron oxide red: 0.00131%, tartrazine: 0.01414%, titanium dioxide: 0.04687%, cobalt oxide: 0.00232%;
- the second layer: poly(methyl methacrylate): 99.9515%, iron oxide red: 0.00098%, tartrazine: 0.01061%, titanium dioxide: 0.03513%, cobalt oxide: 0.00174%;
- the third layer: poly(methyl methacrylate): 99.9677%, iron oxide red: 0.00066%, tartrazine: 0.00707%, titanium dioxide: 0.02344%, cobalt oxide: 0.00116%;
- the fourth layer: poly(methyl methacrylate): 99.9838%, iron oxide red: 0.00033%, tartrazine: 0.00354%, titanium dioxide: 0.01172%, cobalt oxide: 0.00058%.

There could be at most 4 layers.

Comparative Example 3

This comparative example differs from Example 1 in that the mass percentage of the resin powder was 90%, and the mass percentage of the pigment was 10%, and the specific composition is as follows:
- the first layer: poly(methyl methacrylate): 83.3700%, iron oxide red: 0.33703%, tartrazine: 3.63781%, titanium dioxide: 12.05829%, cobalt oxide: 0.59687%;
- the second layer: poly(methyl methacrylate): 84.2015%, iron oxide red: 0.33703%, tartrazine: 3.45592%, titanium dioxide: 11.45538%, cobalt oxide: 0.56703%;
- the third layer: poly(methyl methacrylate): 85.0330%, iron oxide red: 0.30332%, tartrazine: 3.27403%, titanium dioxide: 10.85246%, cobalt oxide: 0.53718%;
- the fourth layer: poly(methyl methacrylate): 85.8645%, iron oxide red: 0.28647%, tartrazine: 3.09214%, titanium dioxide: 10.24955%, cobalt oxide: 0.50734%;
- the fifth layer: poly(methyl methacrylate): 86.6960%, iron oxide red: 0.26962%, tartrazine: 2.91025%, titanium dioxide: 9.64663%, cobalt oxide: 0.47750%;
- the sixth layer: poly(methyl methacrylate): 87.5275%, iron oxide red: 0.25277%, tartrazine: 2.72836%, titanium dioxide: 9.04372%, cobalt oxide: 0.44765%;
- the seventh layer: poly(methyl methacrylate): 88.3590%, iron oxide red: 0.23592%, tartrazine: 2.54647%, titanium dioxide: 8.44081%, cobalt oxide: 0.41781%;
- the eighth layer: poly(methyl methacrylate): 89.1905%, iron oxide red: 0.21907%, tartrazine: 2.36458%, titanium dioxide: 7.83789%, cobalt oxide: 0.38796%;
- the ninth layer: poly(methyl methacrylate): 90.0220%, iron oxide red: 0.20222%, tartrazine: 2.18269%, titanium dioxide: 7.23498%, cobalt oxide: 0.35812%;
- the tenth layer: poly(methyl methacrylate): 90.8535%, iron oxide red: 0.18536%, tartrazine: 2.00080%, titanium dioxide: 6.63206%, cobalt oxide: 0.32828%;

the eleventh layer: poly(methyl methacrylate): 91.6850%, iron oxide red: 0.16851%, tartrazine: 1.81891%, titanium dioxide: 6.02915%, cobalt oxide: 0.29843%;
the twelfth layer: poly(methyl methacrylate): 92.5165%, iron oxide red: 0.15166%, tartrazine: 1.63702%, titanium dioxide: 5.42623%, cobalt oxide: 0.26859%;
the thirteenth layer: poly(methyl methacrylate): 93.3480%, iron oxide red: 0.13481%, tartrazine: 1.45513%, titanium dioxide: 4.82332%, cobalt oxide: 0.23875%;
the fourteenth layer: poly(methyl methacrylate): 94.1795%, iron oxide red: 0.11796%, tartrazine: 1.27323%, titanium dioxide: 4.22040%, cobalt oxide: 0.20890%;
the fifteenth layer: poly(methyl methacrylate): 95.0110%, iron oxide red: 0.10111%, tartrazine: 1.09134%, titanium dioxide: 3.61749%, cobalt oxide: 0.17906%;
the sixteenth layer: poly(methyl methacrylate): 95.8425%, iron oxide red: 0.08426%, tartrazine: 0.90945%, titanium dioxide: 3.01457%, cobalt oxide: 0.14922%;
the seventeenth layer: poly(methyl methacrylate): 96.6740%, iron oxide red: 0.06741%, tartrazine: 0.72756%, titanium dioxide: 2.41166%, cobalt oxide: 0.11937%.

Comparative Example 4

This comparative example differs from Example 1 in that the mass percentage of the resin powder was 99.9994%, and the mass percentage of the pigment was 0.0006%, and the specific composition is as follows:
the first layer: poly(methyl methacrylate): 99.9990%, red iron oxide: 0.00002%, tartrazine: 0.00022%, titanium dioxide: 0.00073%, cobalt oxide: 0.00004%;
the second layer: poly(methyl methacrylate): 99.9991%, red iron oxide: 0.00002%, tartrazine: 0.00021%, titanium dioxide: 0.00069%, cobalt oxide: 0.00003%;
the third layer: poly(methyl methacrylate): 99.9991%, red iron oxide: 0.00002%, tartrazine: 0.00020%, titanium dioxide: 0.00065%, cobalt oxide: 0.00003%;
the fourth layer: poly(methyl methacrylate): 99.9992%, red iron oxide: 0.00002%, tartrazine: 0.00019%, titanium dioxide: 0.00062%, cobalt oxide: 0.00003%;
the fifth layer: poly(methyl methacrylate): 99.9992%, iron oxide red: 0.00002%, tartrazine: 0.00018%, titanium dioxide: 0.00058%, cobalt oxide: 0.00003%;
the sixth layer: poly(methyl methacrylate): 99.9993%, red iron oxide: 0.00002%, tartrazine: 0.00016%, titanium dioxide: 0.00054%, cobalt oxide: 0.00003%;
the seventh layer: poly(methyl methacrylate): 99.9993%, red iron oxide: 0.00001%, tartrazine: 0.00015%, titanium dioxide: 0.00051%, cobalt oxide: 0.00003%;
the eighth layer: poly(methyl methacrylate): 99.9994%, red iron oxide: 0.00001%, tartrazine: 0.00014%, titanium dioxide: 0.00047%, cobalt oxide: 0.00002%;
the ninth layer: poly(methyl methacrylate): 99.9994%, red iron oxide: 0.00001%, tartrazine: 0.00013%, titanium dioxide: 0.00044%, cobalt oxide: 0.00002%;
the tenth layer: poly(methyl methacrylate): 99.9995%, red iron oxide: 0.00001%, tartrazine: 0.00012%, titanium dioxide: 0.00040%, cobalt oxide: 0.00002%;
the eleventh layer: poly(methyl methacrylate): 99.9995%, red iron oxide: 0.00001%, tartrazine: 0.00011%, titanium dioxide: 0.00036%, cobalt oxide: 0.00002%;
the twelfth layer: poly(methyl methacrylate): 99.9996%, red iron oxide: 0.00001%, tartrazine: 0.00010%, titanium dioxide: 0.00033%, cobalt oxide: 0.00002%;
the thirteenth layer: poly(methyl methacrylate): 99.9996%, red iron oxide: 0.00001%, tartrazine: 0.0009%, titanium dioxide: 0.00029%, cobalt oxide: 0.00001%;
the fourteenth layer: poly(methyl methacrylate): 99.9997%, red iron oxide: 0.00001%, tartrazine: 0.00008%, titanium dioxide: 0.00025%, cobalt oxide: 0.00001%;
the fifteenth layer: poly(methyl methacrylate): 99.9997%, red iron oxide: 0.00001%, tartrazine: 0.00007%, titanium dioxide: 0.00022%, cobalt oxide: 0.00001%;
the sixteenth layer: poly(methyl methacrylate): 99.9998%, red iron oxide: 0.00001%, tartrazine: 0.00005%, titanium dioxide: 0.00018%, cobalt oxide: 0.00001%;
the seventeenth layer: poly(methyl methacrylate): 99.9998%, red iron oxide: 0.00000%, tartrazine: 0.00004%, titanium dioxide: 0.00015%, cobalt oxide: 0.00001%.

the performance of the gradient resin obtained in Examples 1-8 and Comparative Examples 1-4 was tested, and the experimental results are shown in Table 1.

In the test, the test standard of luminous transmittance refers to GB2410-2008, and the test method is as follows: a sample with a size of 30 mm×30 mm×1 mm was prepared, and tested by a haze meter.

The test standard of flexural strength refers to ISO 10477-2018, and the test method is as follows:

Three-point flexural test: 5 strength bars of (2±0.1 mm)× (2±0.1 mm)×(25±1 mm) were cut for the flexural strength test. The inspector put the strength bar on an electric tensile testing apparatus for testing, and the spacing was 20 mm; the load was applied at a loading rate of 1±0.1 mm/min until the sample fractured; the 5 samples were tested respectively, and the strength value of each sample was recorded, and taken the average value.

The test standard of Vickers hardness refers to GB/T4340.1-2009, and the test method is as follows:

Three-point test: the finished product piece was placed on a Vickers hardness tester for testing, and hardness values at three different positions were measured and taken the average value.

Water absorption value and solubility value refers to ISO 10477-2018, and the test method is as follows:

5 test round pieces with a size of φ15±1 mm*(1.0±0.2) mm were prepared. 2000-grit sandpaper was used for water polishing, and a caliper was used to measure the diameter and thickness of the samples to an accuracy of 0.01 mm. The sample volume was calculated and expressed in mm$^3$.

1) The samples were placed in a desiccator and dried in an oven at 37° C. After 22 h, the samples were placed in another desiccator at 23±2° C. for 2 h. Then, one by one, the samples were taken out and weighed with a ten-thousandth balance to an accuracy of 0.1 mg. The above steps were continued until a constant weight was reached, which was denoted as $m_1$;
2) The samples were taken out and stored in 20 mL water (constant-temperature water bath) at 37±1° C. for 7 d, then taken out, washed with water, wiped for water on the surface and then tested, the samples were weighed with a ten-thousandth balance, and the mass was denoted as $m_2$; and 3) The samples were placed into an oven at 37° C. for 14-21 d until the weight kept constant, and then weighed with a ten-thousandth balance, and the mass was denoted as $m_3$.

Calculation of Water Absorption Value

The water absorption values ρws of 5 samples are calculated separately according to formula (1) with a unit of μg/mm³ to an accuracy of 0.1 μg/mm³:

$$\Sigma ws=((m_2-m_3))/V \qquad \text{formula (1)}$$

In formula (1):
$m_2$—the mass of the sample after being soaked in water for 7d with a unit of micrograms (m);
$m_3$—the constant mass of the sample after being soaked in water for 7d with a unit of micrograms (m);
V—the sample volume with a unit of cubic millimeters (mm³).

Calculation of Solubility Value

The solubility value ρsl of 5 samples are calculated separately according to formula (2) with a unit of μg/mm³ to an accuracy of 0.1 m/mm³:

$$\rho s_1=(m_1-m_3)/V \qquad \text{formula (2)}$$

in the formula:
$m_1$—the constant mass of the sample before being soaked in water with a unit of micrograms (μg);
$m_3$—the constant mass of the sample after being soaked in water for 7d with a unit of micrograms (μg);
V—the sample volume with a unit of cubic millimeters (mm³).

The particle size of poly(methyl methacrylate) is too large in Example 5, resulting in that the pigment will be prevented from entering the powder inside, and the prepared disc will have non-uniform color.

The molecular mass of poly(methyl methacrylate) is too small in Example 6, resulting in that the overall molecular mass of the product obtained from press molding will be too low, and the polymer with low molecular mass will be too much, which can be easily dissolved in the mouth.

The molecular mass of poly(methyl methacrylate) is too large in Example 7, resulting in that the raw material cannot be melted and press-molded due to the excessively high hardness.

The resin powder is replaced with polyether ether ketone in Example 8, resulting in that the melting and pressing cannot be achieved with the same process.

The color transition change range between two adjacent layers is too small in Comparative Example 1, resulting in that the incisal of the tooth will have a dark color, and the incisal-edge effect of light incisal-edge color cannot be obtained.

The color transition change range between two adjacent layers is too large in Comparative Example 2, resulting in that the color will show stratification and cannot transition naturally.

The mass percentage of the resin powder is too small in Comparative Example 3, resulting in that the pigment content will be too high, the color will be too dark, and the tooth color consistent with the color guide cannot be customized.

TABLE 1

|  | Luminous Transmittance (%) | Flexural strength (MPa) | Vickers Hardness (HV) | Water Absorption Value (μg/mm³) | Solubility value (μg/mm³) |
| --- | --- | --- | --- | --- | --- |
| Example 1 | 62.6 | 110.7 | 24.5 | 20.3 | 1.2 |
| Example 2 | 63.2 | 114.6 | 22.3 | 21.6 | 1.0 |
| Example 3 | 58.9 | 136.2 | 25.7 | 18.3 | 0.7 |
| Example 4 | 56.3 | 112.6 | 24.3 | 20.6 | 1.3 |
| Example 5 | 63.2 | 111.9 | 23.9 | 19.9 | 1.1 |
| Example 6 | 63.1 | 90.4 | 18.3 | 24.2 | 8.5 |
| Example 7 | / | / | / | / | / |
| Example 8 | / | / | / | / | / |
| Comparative Example 1 | 62.5 | 110.7 | 24.5 | 20.3 | 1.2 |
| Comparative Example 2 | 62.6 | 110.2 | 24.3 | 20.1 | 1.1 |
| Comparative Example 3 | 62.4 | 110.6 | 24.5 | 20.3 | 1.2 |
| Comparative Example 4 | 64.7 | 110.5 | 24.4 | 20.2 | 1.3 |

As can be seen from Table 1, the gradient resin product obtained in the present application has no layer stratification; the color transition is natural, the layers merge into each other, no transition boundary can be found between layers, the interlayer color transition change range is 0.1%-20%, and it is invisible to the naked eye; the prepared gradient resin has a luminous transmittance of 55-65%, a flexural strength of more than 100 MPa, a Vickers hardness of more than 20 HV, a water absorption value of less than 25 μg/mm³, and a solubility value of less than 5 μg/mm³.

The particle size of poly(methyl methacrylate) is too small in Example 4, which will cause cracks during pressing.

The mass percentage of the resin powder is too large in Comparative Example 4, resulting in that the pigment content will be low, the color will be too light, and the tooth color consistent with the color guide cannot be customized.

Although the detailed process equipment and process flow of the present application are described through the above embodiments, the present application is not limited to the above detailed process equipment and process flow, which means that the present application is not necessarily rely on the above detailed process equipment and process flow to be implemented.

Although the optional embodiments of the present application are described in detail herein, the present application is not limited to the specific details of the above embodiments.

In addition, it should be noted that the specific technical features described in the above specific embodiments can be combined in any suitable manner unless they are inconsistent. The combination method will not be specified otherwise to avoid repetition.

What is claimed is:

1. A gradient resin, which is formed by merging different layers with color transition change and wherein by mass percentage, raw materials from which the gradient resin is prepared are composed of 98-99.99% of a resin powder and 0.01-2% of a pigment;

wherein a change percentage of a mass content of the pigment in the raw materials between two adjacent layers is 5-20%;

wherein a particle size of the resin powder in the raw materials is 0.1-200 μm; and wherein the resin powder comprises any one or a mixture of at least two of poly(methyl methacrylate), poly(ethyl methacrylate), poly(propyl methacrylate), poly(n-butyl methacrylate), poly(isobutyl methacrylate), poly(hexyl methacrylate), poly(dicyclopentenyl methacrylate), poly(tetrahydrofurfuryl methacrylate), poly(2-hydroxyethyl methacrylate), poly(glycidyl methacrylate), poly(lauryl methacrylate), poly(cyclohexyl methacrylate), poly(benzyl methacrylate), poly(allyl methacrylate), poly(2-ethoxyethyl methacrylate), methoxy polyethylene glycol methacrylate, poly(glycerol methacrylate), poly(isobornyl methacrylate), polyvinyl chloride, polystyrene, polyoxymethylene, polyacetaldehyde and polyurethane;

wherein the gradient resin has a luminous transmittance of more than or equal to 50%, a flexural strength of more than 100 MPa, a Vickers hardness of more than 20 HV, a water absorption value of less than 25 μg/mm$^3$, and a solubility value of less than 5 μg/mm$^3$.

2. The gradient resin according to claim 1, wherein a molecular mass of the resin powder in the raw materials is 100000-1000000.

3. The gradient resin according to claim 2, wherein the molecular mass of the resin powder in the raw materials is 300000-700000.

4. The gradient resin according to claim 1, wherein a particle size of the resin powder in the raw materials is 30-150 μm.

5. The gradient resin according to claim 1, wherein the pigment comprises any one or a mixture of at least two of zirconium vanadium yellow, cerium praseodymium yellow, tartrazine, ferric oxide yellow, chrome yellow, sunset red, iron oxide red, erbium oxide, titanium dioxide, cobalt oxide, chromium oxide, iron oxide brown, iron oxide black and carbon black.

6. The gradient resin according to claim 2, wherein the molecular mass of the resin powder in the raw materials is 400000-600000.

7. The gradient resin according to claim 1, wherein a particle size of the resin powder in the raw materials is 40-100 μm.

8. A preparation method for the gradient resin according to claim 1, comprising:

1) Preparing colored powders: weighing and uniformly mixing the pigment and the resin powder for preparing colored powders with different colors according to respective color formulas, and weighing and proportioning the colored powders for each layer according to a layer configuration;

2) spreading the materials: adding the colored powders with different colors obtained in step 1) into a molding mold in sequence, spreading one colored powder flat out in the molding mold, then adding another colored powder of the next layer and spreading the colored powder flat out until all the colored powders have been added; and 3) Performing a press molding: subjecting the mold to a hot-press molding, and taking the mold out after cooling, so as to obtain the gradient resin.

9. The preparation method according to claim 8, wherein, in step 2), the color transition change range between two adjacent layers is 0.1-20%;

optionally, in step 3), a temperature of the hot-press molding is 60-220° C.;

optionally, in step 3), a pressure of the hot-press molding is 1-20 MPa.

10. The preparation method according to claim 8, wherein the preparation method further comprises a pretreatment step for the resin powder before step 1);

optionally, the pretreatment comprises drying, a temperature of the drying is 80-100° C., and a time of the drying is 1-3 h.

11. The preparation method according to claim 8, comprising:

1) Preparing colored powders: drying the resin powder at 80-100° C. for 1-3 h, weighing and uniformly mixing the pigment and the resin powder for preparing colored powders with different colors according to respective color formulas, and weighing and proportioning the colored powders for each layer according to a layer configuration;

2) spreading the materials: adding the colored powders with different colors obtained in step 1) into a molding mold in sequence, spreading one colored powder flat out in the molding mold, then adding another colored powder of the next layer and spreading the colored powder flat out until all the colored powders have been added, wherein the color transition change range between two adjacent layers is 0.1-20%; and 3) Performing a press molding: subjecting the materials to be molded to a press molding in the mold, and removing the mold after molding, so as to obtain the gradient resin with natural interlayer transition and no color stratification, wherein an optional press method is a hot-press molding, and the mold is removed after cooling, a temperature of the hot-press molding is 60-220° C., and a pressure of the hot-press molding is 1-20 MPa.

12. The preparation method according to claim 8, wherein, in step 3), a temperature of the hot-press molding is 100-180° C.

13. The preparation method according to claim 8, wherein, in step 3), a temperature of the hot-press molding is 120-160° C.

14. The preparation method according to claim 8, wherein, in step 3), a pressure of the hot-press molding is 4-15 MPa.

15. The preparation method according to claim 8, wherein, in step 3), a pressure of the hot-press molding is 8-12 MPa.

16. A method for preparing a gradient dental restoration by using the gradient resin according to claim 1.

* * * * *